(12) United States Patent
Liu et al.

(10) Patent No.: US 8,172,461 B2
(45) Date of Patent: May 8, 2012

(54) GRID ASSEMBLY POSITIONING CIRCUIT AND DETECTOR ASSEMBLY INCLUDING THE SAME

(75) Inventors: James Zhengshe Liu, Glenview, IL (US); Rowland Frederick Saunders, Hartland, WI (US); Jon Charles Omernick, Wauwatosa, WI (US); Rajendra Shirish Jadhav, Brookfield, WI (US); Huayi Wang, Beijing (CN); Gary Vernon McBroom, Dousman, WI (US)

(73) Assignee: General Electric Company, Schenectady, NY (US)

( * ) Notice: Subject to any disclaimer, the term of this patent is extended or adjusted under 35 U.S.C. 154(b) by 191 days.

(21) Appl. No.: 12/550,881

(22) Filed: Aug. 31, 2009

(65) Prior Publication Data
US 2011/0051902 A1    Mar. 3, 2011

(51) Int. Cl.
*G21K 1/00*    (2006.01)
(52) U.S. Cl. .................... 378/205; 378/114; 378/154
(58) Field of Classification Search ............. 378/154, 378/155, 205, 114
See application file for complete search history.

(56) References Cited

U.S. PATENT DOCUMENTS

| | | | |
|---|---|---|---|
| 4,970,463 A * | 11/1990 | Wolf et al. | 324/207.2 |
| 5,684,850 A * | 11/1997 | Warburton et al. | 378/53 |
| 7,342,998 B2 | 3/2008 | Kump et al. | |
| 7,429,737 B2 | 9/2008 | Wojcik et al. | |
| 7,488,946 B2 | 2/2009 | Hennessy et al. | |
| 2002/0090055 A1* | 7/2002 | Zur et al. | 378/154 |
| 2003/0026387 A1* | 2/2003 | Makila et al. | 378/168 |
| 2007/0140424 A1 | 6/2007 | Serceki | |
| 2008/0240358 A1 | 10/2008 | Utschig et al. | |
| 2009/0129547 A1 | 5/2009 | Jabri et al. | |
| 2010/0002831 A1* | 1/2010 | Maack | 378/154 |

FOREIGN PATENT DOCUMENTS

| | | | |
|---|---|---|---|
| JP | 2001154300 A | * | 6/2001 |
| JP | 2006280517 A | * | 10/2006 |

* cited by examiner

*Primary Examiner* — Glen Kao
(74) *Attorney, Agent, or Firm* — The Small Patent Law Group; Dean D. Small (57) ABSTRACT

An x-ray grid alignment circuit for coupling an x-ray grid to a detector includes a marker configured to be mounted to the x-ray grid, a sensor configured to be mounted to the detector, the sensor generating an alignment signal based on a position of the marker, and an alignment module configured to receive the alignment signal from the sensor and utilize the alignment signal to determine if the x-ray grid is coupled to a detecting face of the detector. A detector assembly including the x-ray grid alignment circuit and a method of coupling an x-ray grid to a detector are also provided.

24 Claims, 9 Drawing Sheets

GRID ASSEMBLY POSITIONING CIRCUIT AND DETECTOR ASSEMBLY INCLUDING THE SAME

BACKGROUND OF THE INVENTION

The subject matter disclosed herein relates generally to imaging detectors, and more particularly to a circuit for positioning a grid assembly on a portable imaging detector.

In various medical imaging applications, a portable imaging detector may be utilized to perform medical imaging. At least one conventional portable x-ray detector includes an external casing that is typically formed of metal. The external casing includes a front cover, a back cover, and a plurality of sides that together form the external casing. The portable x-ray detector also includes a plurality of detector elements that are disposed proximate to the portable x-ray device front cover. During operation, x-rays pass through the front cover and impinge on the plurality of detector elements. The detector elements produce an electrical signal that represents the intensity of the impinging X-ray beam and hence allows estimation of the attenuation of the beam as the beam passes through the object.

During some imaging procedures, it is desirable to utilize an x-ray grid with the portable detector to reduce x-ray scattering. To utilize the x-ray grid with the portable x-ray detector, the x-ray grid is coupled to the portable detector. However, it is often difficult for an operator to properly couple the x-ray grid to the portable detector. More specifically, the portable detector casing is typically symmetrical making it difficult for an operator to distinguish the front cover from the back cover. Therefore, in some instances, the operator may improperly attach the x-ray grid to the back cover, e.g. the non-detecting face.

BRIEF DESCRIPTION OF THE INVENTION

In one embodiment, an x-ray grid alignment circuit for coupling an x-ray grid to a detector is provided. The x-ray grid alignment circuit includes a marker configured to be mounted to the x-ray grid, a sensor configured to be mounted to the detector, the sensor generating an alignment signal based on a position of the marker, and an alignment module configured to receive the alignment signal from the sensor and utilize the alignment signal to determine if the x-ray grid is coupled to a detecting face of the detector.

In another embodiment, a detector assembly including a portable detector and an x-ray grid configured to couple to the portable detector is provided. The detector assembly also includes an x-ray grid alignment circuit. The x-ray grid alignment circuit includes a marker configured to be mounted to the x-ray grid, a sensor configured to be mounted to the detector, the sensor generating an alignment signal based on a position of the marker, and an alignment module configured to receive the alignment signal from the sensor and utilize the alignment signal to determine if the x-ray grid is coupled to a detecting face of the detector.

In a further embodiment, a method for coupling an x-ray grid to a portable detector is provided. The method includes providing a portable detector, providing an x-ray grid configured to couple to the portable detector, providing a positioning assembly that includes a marker configured to be mounted to the x-ray grid and a sensor configured to be mounted to the detector, the sensor generating an alignment signal based on a position of the marker, determining if the x-ray grid is coupled to a detecting face of the portable detector based on the alignment signal, and displaying an indication on a display when the x-ray grid is coupled to the detecting face of the portable detector.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 1:
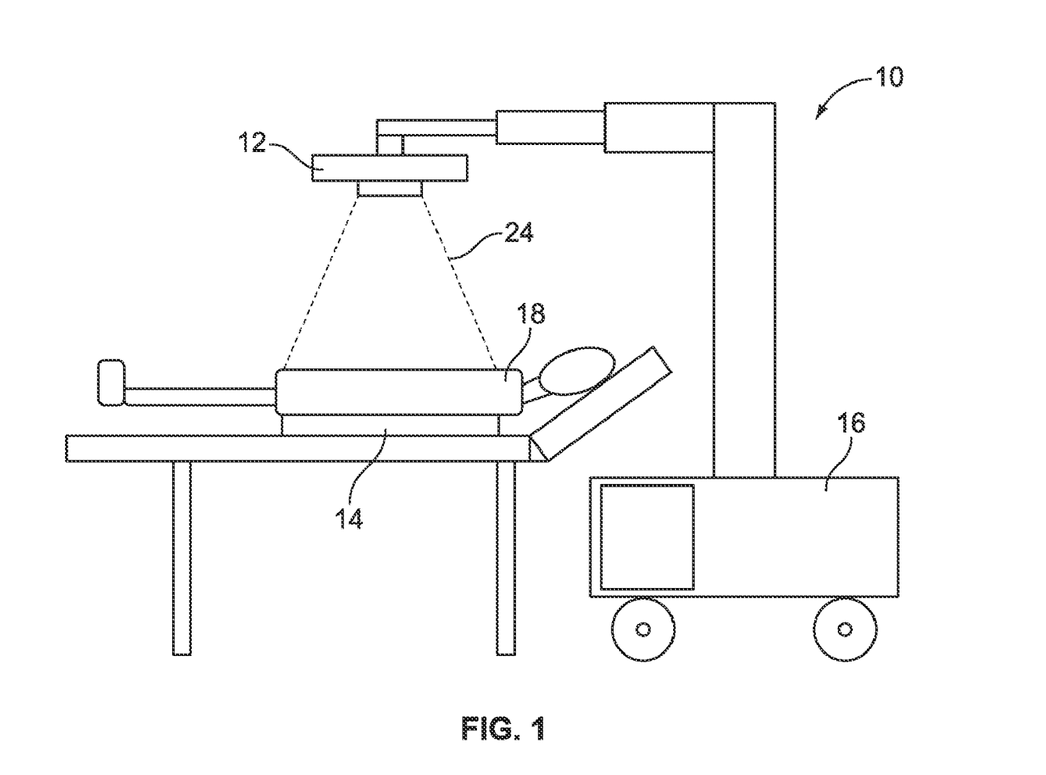
FIG. 1 is a pictorial view of an exemplary medical imaging system in accordance with an embodiment of the present invention.
Figure 2:
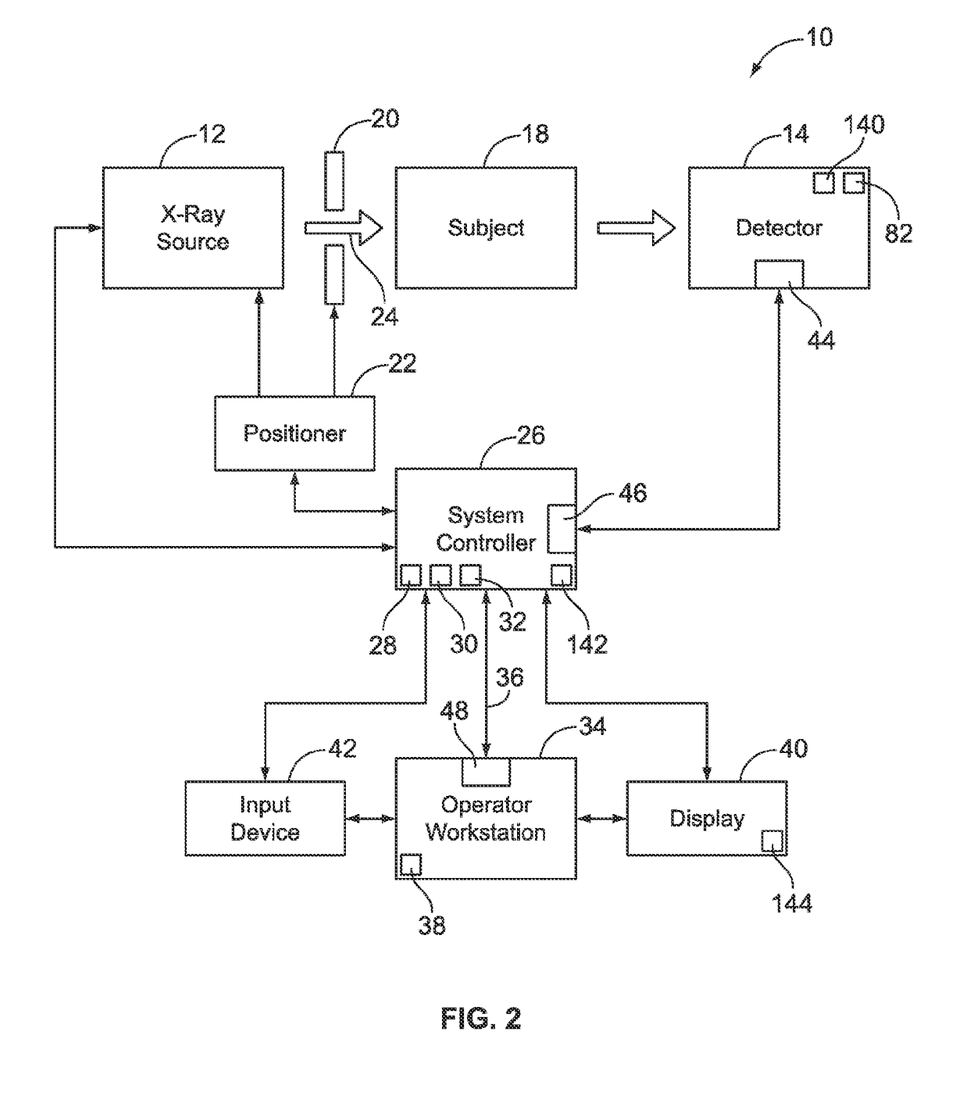
FIG. 2 is a block schematic diagram of the exemplary medical imaging system shown in FIG. 1 in accordance with an embodiment of the present invention.

Referring to the drawings, FIG. 1 is a pictorial view of an exemplary imaging system 10 in accordance with an embodiment of the present invention. FIG. 2 is a block schematic diagram of the exemplary imaging system 10 shown in FIG. 1 in accordance with an embodiment of the present invention. Various embodiments of the invention may be used with the exemplary medical imaging system 10 as shown in FIG. 1. The medical imaging system 10 may be any type imaging system, for example, different types of medical imaging systems, such as an x-ray imaging system, a tomosynthesis imaging system, a Positron Emission Tomography (PET), a Single Photon Emission Computed Tomography (SPECT), a Computed Tomography (CT), an ultrasound system, Magnetic Resonance Imaging (MRI) or any other system capable or generating medical images. Moreover, the various embodiments are not limited to medical imaging systems for imaging human subjects, but may include veterinary or non-medical systems for imaging non-human objects, or non-destructive testing systems (e.g. airport baggage systems) etc.

The medical imaging system 10 in the preferred embodiment is a digital radiography imaging system 10 that includes an x-ray source 12 and a detector 14. As shown in FIG. 1, the x-ray source 12 is mounted to a gantry 16. In the exemplary embodiment, the gantry 16 is movable to enable the x-ray source 12 to be properly positioned with respect to a subject 18 being imaged or to enable the x-ray source 12 to be moved from one imaging room to another. Optionally, the gantry 16 is stationarily mounted by coupling the gantry to a floor, for example. Referring to FIG. 2, the imaging system 10 may also include a collimator 20 that is disposed between the x-ray source 12 and the subject 18. The imaging system 10 may also include a positioner 22. The positioner 22 is a mechanical controller coupled to the x-ray source 12 and collimator 20 for controlling the positioning of the x-ray source 12 and the collimator 20.

During operation, the imaging system 10 generates images of the subject 18 by means of an x-ray beam 24 emitted by the x-ray source 12, and passing through the collimator 20. The collimator 20 forms and confines the x-ray beam 24 to a desired region, wherein the subject 18, such as a human patient, an animal or an object, is positioned. A portion of the x-ray beam 24 passes through or around the subject 18 and, being altered by attenuation and/or absorption by tissues within the subject 18, continues on toward and impacts the detector 14. In one embodiment, the detector 14 may be a fixed detector that is mounted in a fixed position. In the exemplary embodiment, the detector 14 is a portable digital flat panel x-ray detector. During operation, the detector 14 converts x-ray photons received on its surface to lower energy light photons, and subsequently to electric signals, which are acquired and processed to reconstruct an image of internal anatomy of the subject 18.

The imaging system 10 further includes a system controller 26 coupled to the x-ray source 12, the detector 14, and the positioner 22 for controlling operation of the x-ray source 12, the detector 14, and the positioner 22. The system controller 26 may supply both power and control signals for imaging examination sequences. In general, the system controller 26 controls the operation of the imaging system to execute examination protocols and to process acquired image data. The system controller 26 may also include signal processing circuitry, based on a general purpose or application-specific computer, associated memory circuitry for storing programs and routines executed by the computer, as well as configuration parameters and image data, interface circuits, and so forth.

The system controller 26 may further include at least one computer or processor 28 that configured to coordinate the operation of the x-ray source 12, the detector 14, and the positioner 22, and to process image data acquired from the detector 14. As used herein, the term "computer" or may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 28 carries out various functionality in accordance with routines stored in an associated memory circuitry 30. The associated memory circuitry 30 may also serve to store configuration parameters, imaging protocols, operational logs, raw and/or processed image data, and so forth.

The system controller 26 may further include interface circuitry 32 that permits an operator or user to define imaging protocols, imaging sequences, determine the operational status and health of system components, and so-forth. The interface circuitry 32 may allow external devices to receive images and image data, and command operation of the radiography system, configure parameters of the system, and so forth.

The system controller 26 may be coupled to a range of external devices via a communications interface. Such devices may include, for example, an operator workstation 34 for interacting with the system controller 26 or directly to the imaging system, processing or reprocessing images, viewing images, and so forth. The operator workstation 34 may be embodied as a personal computer (PC) that is positioned near the imaging system 10 and hard-wired to the system controller 26 via a communication link 36. The workstation 34 may also be embodied as a portable computer such as a laptop computer or a hand-held computer that transmits information to the system controller 26. In one embodiment, the communication link 36 may be hardwired between the system controller 26 and the workstation 34. Optionally, the communication link 36 may be a wireless communication link that enables information to be transmitted to or from the workstation to the system controller 26 wirelessly. In the exemplary embodiment, the workstation 34 controls real-time operation of the imaging system 10. The workstation 34 is also programmed to perform medical image diagnostic acquisition and reconstruction processes described herein.

Accordingly, the operator workstation 34 includes a central processing unit (CPU) or computer 38, a display 40 and an input device 42. In the exemplary embodiment, the computer 38 executes a set of instructions that are stored in one or more storage elements or memories, in order to process input data. The storage elements may also store data or other information as desired or needed. The storage element may be in the form of an information source or a physical memory element within the computer 38. The set of instructions may include various commands that instruct the computer or processor 38 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 38 connects to the communication link 36 and receives inputs, e.g., user commands, from the input device 42. The input device 42 may be, for example, a keyboard, mouse, a touch-screen panel, and/or a voice recognition system, etc. Through input device 42 and associated control panel switches, the operator can control the operation of the imaging system 10 and the positioning of the x-ray source 12 for a scan. Similarly, the operator can control the display of the resulting image on the display 40 and can perform image-enhancement functions using programs executed by the workstation CPU 38. The workstation 34 may also be linked to the system controller 26 by any one or more network links.

In the exemplary embodiment, to transmit the electric signals from the detector 14 to the system controller 26 or the workstation 34, the detector 14 includes a transceiver 44 that is configured to transmit the electrical signals and other information generated by the detector 14 in a wireless format to a corresponding transceiver 46 that is mounted in the system controller 26. Optionally, the transceiver 44 is configured to transmit the electrical signals and other information generated by the detector 14 in a wireless format to a corresponding transceiver 48 that is mounted in the workstation 34.

Figure 3:
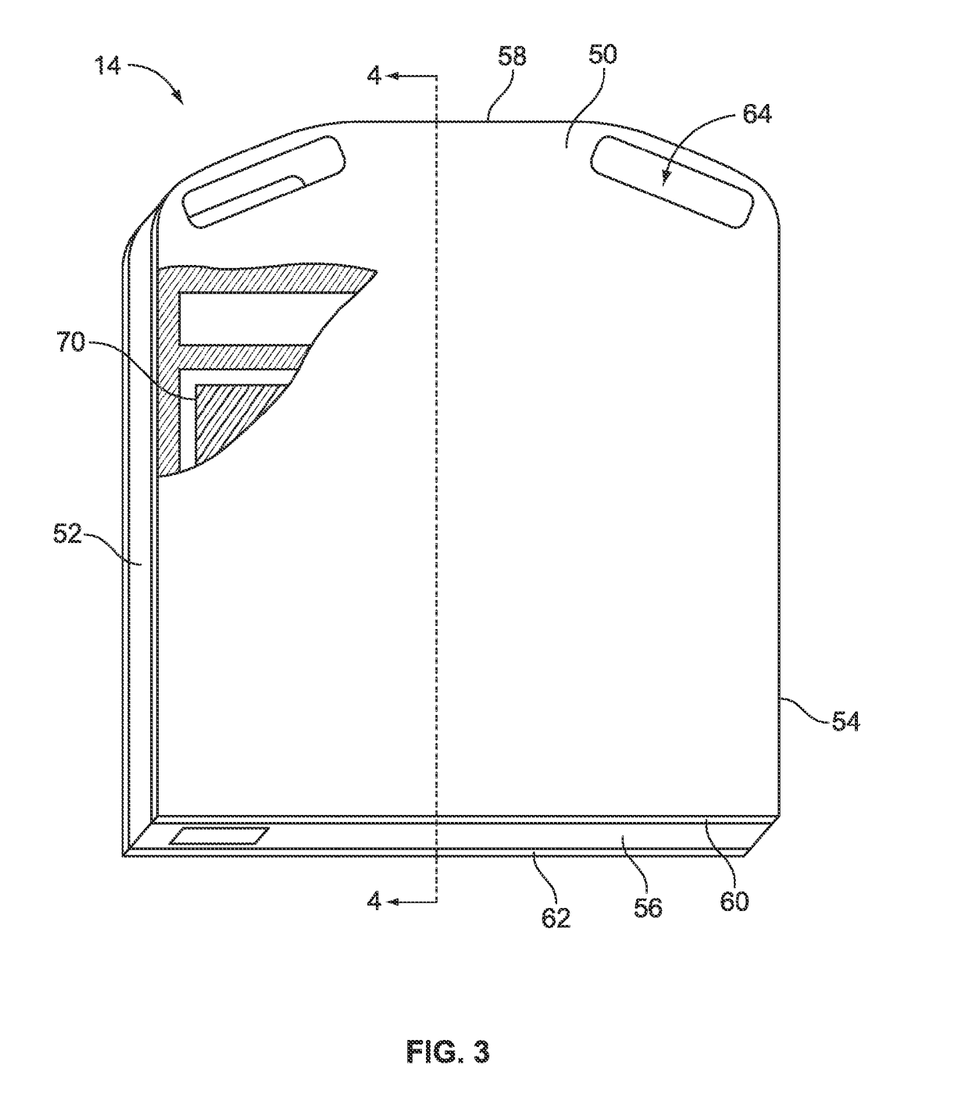
FIG. 3 is a top cut-away view of the exemplary x-ray detector shown in FIGS. 1 and 2 in accordance with an embodiment of the present invention.

FIG. 3 is a bottom cut-away view of the exemplary portable detector 14 shown in FIGS. 1 and 2. In the exemplary embodiment, the portable detector 14 is hand-carried by an operator to various locations to perform medical imaging. Additionally, the portable detector 14 may be mounted on a wheeled cart or other movable apparatus to enable an operator to move the detector 14 from one location to another location.

As shown in FIG. 3, the portable detector 14 includes a casing 50. The casing 50 is formed to include a pair of sidewalls 52 and 54, a bottom side 56, and an opposing top side 58. The casing 50 also includes a front cover 60, shown as a surface parallel to the plane of the illustration, and an opposing back cover 62. The casing also includes a slot 64 that extends from the front cover 60 to the back cover 62. During operation, the slot 64 functions as a handle to enable an operator to transport the portable detector 14. Specifically, the slot 64 can be used to mount, carry and/or store the portable detector 14. The sidewalls, top and bottom walls, the front and back covers together form the casing 50. The casing 50 may be made of a lightweight, low atomic number (N) material, such as aluminum, or a graphite material. Graphite has a lower weight than aluminum, but it is also stiffer and less energy-absorbent.

Figure 4:
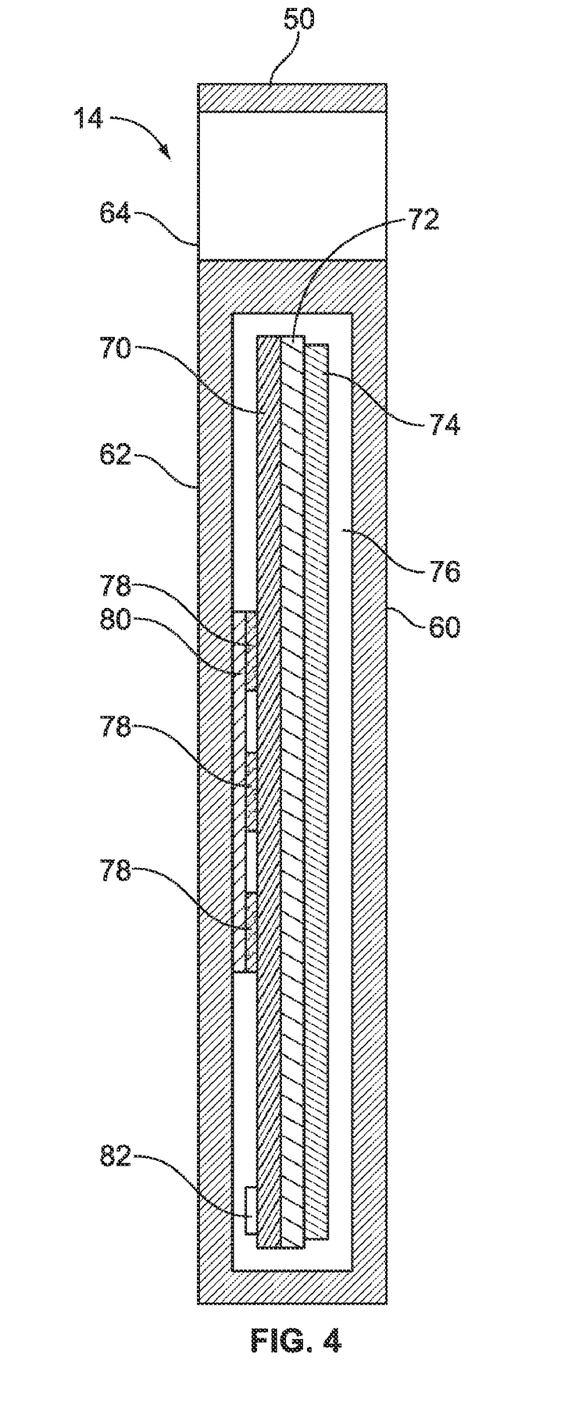
FIG. 4 is a side cut-away view of the detector shown in FIG. 3 in accordance with an embodiment of the present invention.

FIG. 4 is a side cut-away view of the portable detector 14 shown in FIG. 3 viewed along the line 4-4 of FIG. 3. As shown in FIG. 4, the detector 14 also includes a circuit board 70 that is affixed (e.g., using an adhesive) to a panel support 72 that may be fabricated from a low N material, which in turn is affixed to a panel 74. The panel 74 may be a glass panel and may include x-ray scintillator material. In the exemplary embodiment, the panel 74 includes a plurality of scintillators. As such, during operation, the panel 74 is formed to include a plurality of detector rows that each include a plurality of detector elements (not shown), that together sense the projected x-rays that pass through an object, such as a patient. During operation, each detector element produces an electrical signal that represents the intensity of an impinging X-ray beam and hence allows estimation of the attenuation of the beam as the beam passes through the subject 18. In some embodiments, the panel support 72 is not used, and circuit board 70 is affixed directly to the panel 74. Together, circuit board 70 and panel 74 (and panel support 72, if present) comprise an "electronic assembly."

To provide some degree of break resistance for panel 74, a gap 76 is provided between the panel 74 and the front cover 60. Also, the electronic assembly is clear of any wall of the casing, but is mounted to the back cover 62. Additionally, heat generating components 78 on the circuit board 70 may be thermally coupled to back cover 62 using a heat conducting compound 80. The heat conducting compound 80 provides, directly or indirectly, a mechanical coupling between the circuit board 70 and the back cover 62. In the exemplary embodiment, the portable detector 14 also includes a processor 82. In the exemplary embodiment, the processor 82 is mounted to the circuit board 70. The processor 82 is configured to store information to operate the portable detector 14 and/or to transmit information to a remote location via the wireless transceiver 44 as discussed above.

In the exemplary embodiment, the detector 14 is portable, but typically large enough to image a significant region of a human patient, such as a patient's chest. Thus, the portable detector 14 may be only about one or a few centimeters in thickness, but may be tens of centimeters in width and length. To become familiar with the problems associated with coupling an x-ray grid to a portable detector, such as the detector 14 shown in FIGS. 1-4, reference is now made to FIG. 5.

Figure 5:
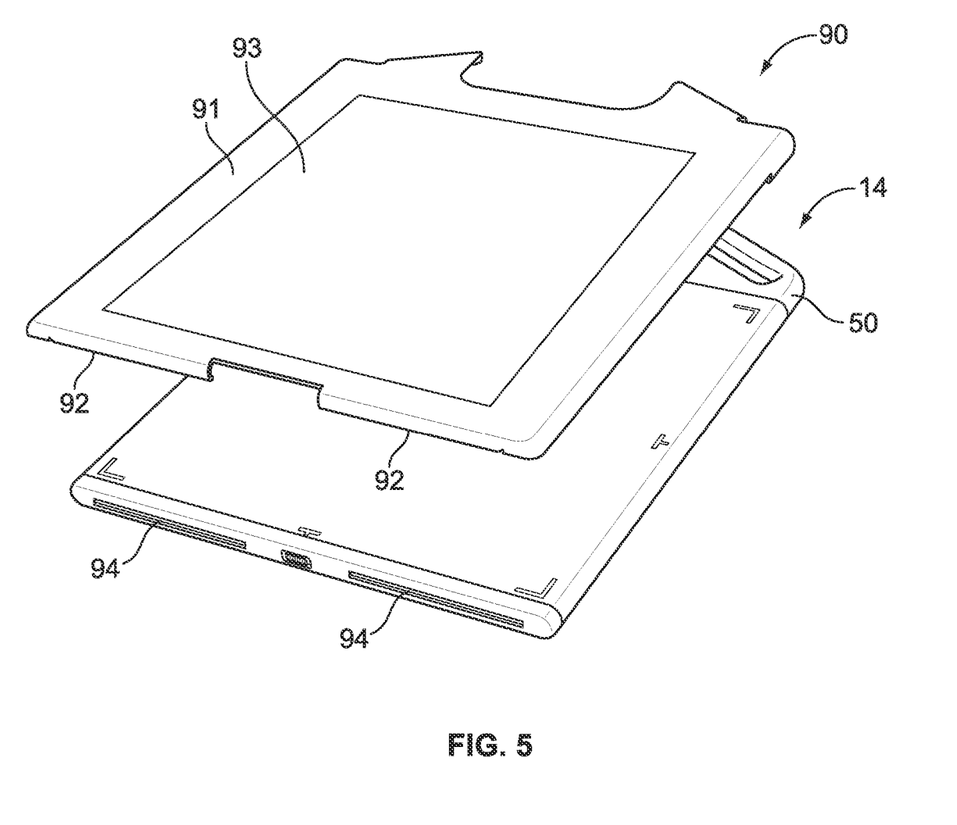
FIG. 5 is a top perspective view of the portable detector shown in FIGS. 1-4 and an exemplary x-ray grid that is configured to be coupled to the portable detector in accordance with an embodiment of the present invention.
Figure 6A:
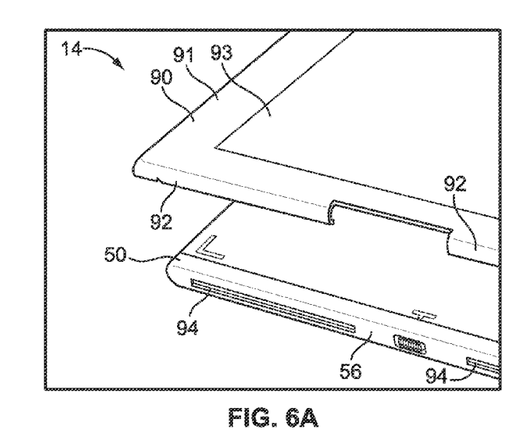
FIGS. 6A-6C are perspective views of the portable detector and x-ray grid shown in FIG. 5.
Figure 6B:
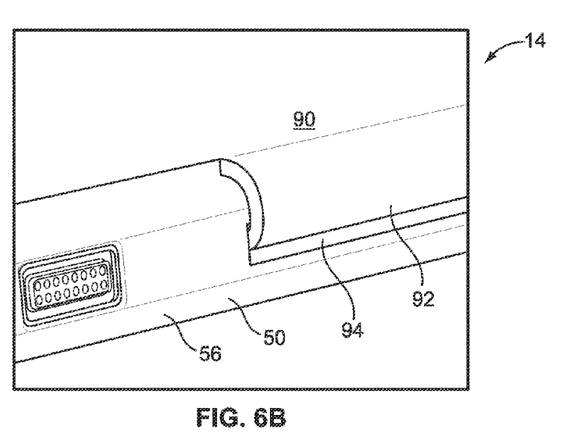
Figure 6C:
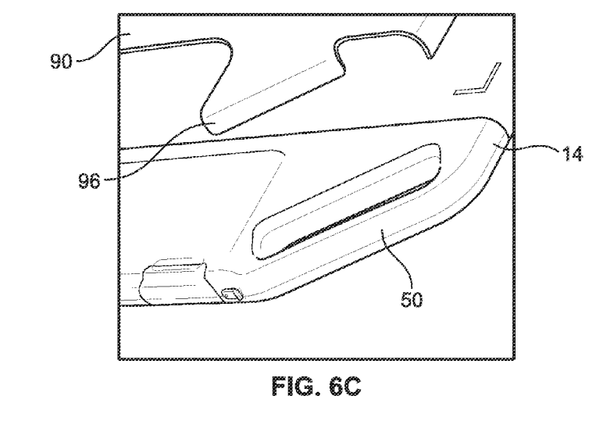

FIG. 5 is a top perspective view of the portable detector 14 and an exemplary x-ray grid assembly 90 that is configured to be coupled to the portable detector 14. In the exemplary embodiment, the x-ray grid assembly 90 is fabricated to include a grid holder 91 and an x-ray grid 93. The grid holder 91 is configured to enable the x-ray grid 93 to be coupled securely to the detector 14. The x-ray grid 93 may be an anti-scatter grid, e.g. a Bucky grid, or some other grid appropriate for medical x-ray imaging. To enable the x-ray grid assembly 90 to be coupled to the detector 14, the x-ray grid assembly 90 includes several features that enable the x-ray grid holder 91 to be snap fit to the portable detector 14. As shown in FIGS. 6A and 6B, in the exemplary embodiment, the x-ray gird holder 91 includes a plurality of tabs 92 that are configured to be snapped into respective slots 94 that are formed in the detector casing 50. In the exemplary embodiment, the slots 94 are formed in the detector casing bottom side 56. As shown in FIG. 6C, the x-ray grid holder 91 also includes at least two flexible coupling devices 96. The coupling devices 96 are configured to bias outwardly away from the detector casing 50 when the x-ray grid holder 91 is coupled to the detector 14. After the x-ray grid assembly 90 is coupled to the detector 14, the devices 96 flex inwardly to at least partially circumscribe the casing 50. When the tabs 92 are inserted into the slots 94 and the coupling devices are properly attached to the casing 50, the x-ray grid 90 is coupled to the detector 14.

As discussed above, because of the symmetrical configuration of the detector 14, it is often difficult for an operator to properly couple the x-ray grid assembly 90 to the portable detector 14. More specifically, the portable detector casing 50 is generally symmetrical making it difficult for an operator to distinguish the front cover 60 from the back cover 62. Therefore, in some instances, the operator may improperly attach the x-ray grid assembly 90 to the back cover 62, e.g. the non-detecting face. To enable the operator and/or the imaging system 10 to determine when the x-ray grid assembly 90 is coupled to the detecting face, e.g. the front cover 60 to the portable detector 14, the portable detector 14 includes an x-ray grid alignment circuit 100 for coupling the x-ray grid assembly 90 to the detector 14.

Figure 7:
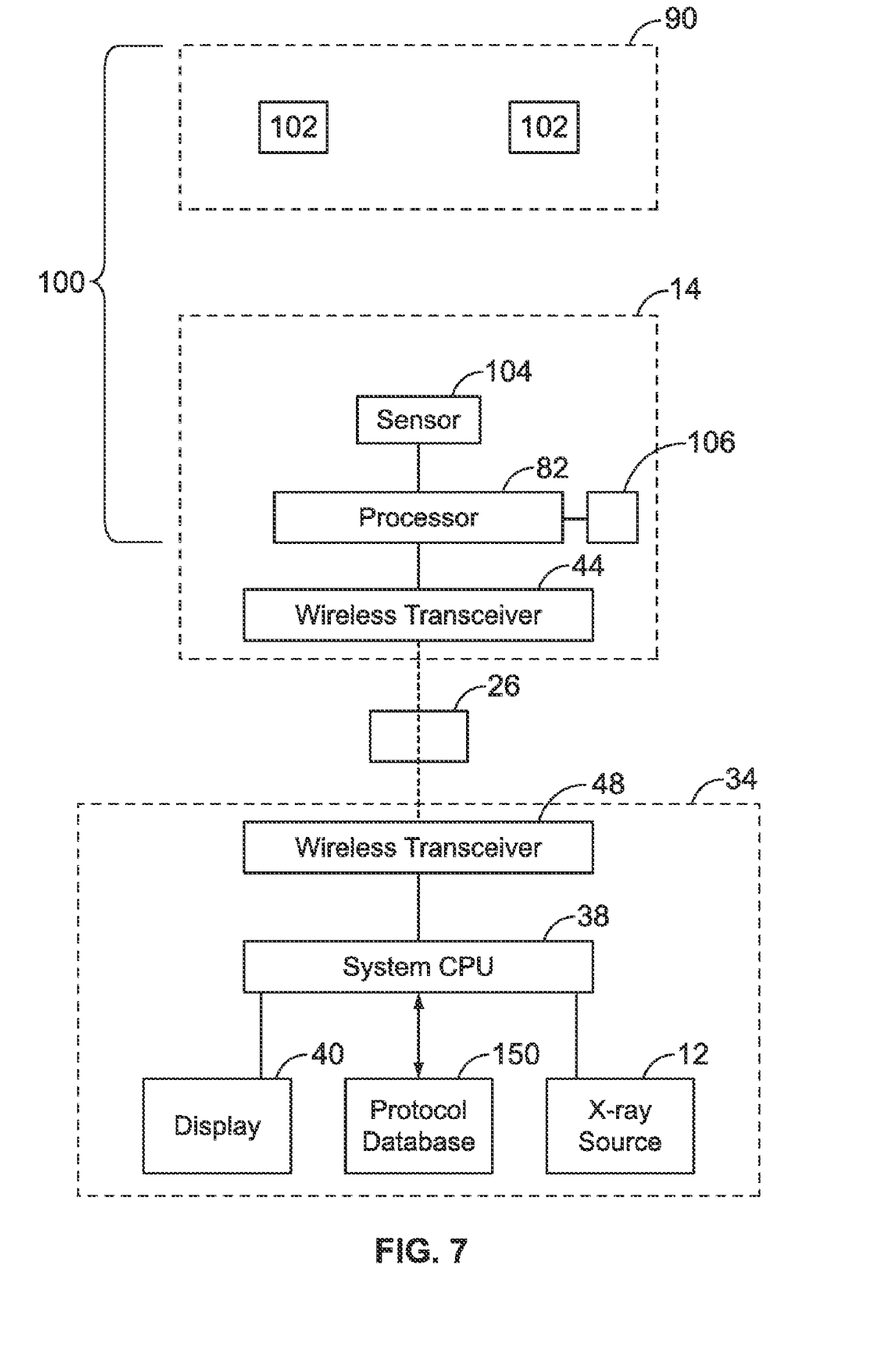
FIG. 7 is a schematic illustration of an exemplary x-ray grid alignment circuit in accordance with an embodiment of the present invention.

FIG. 7 is a schematic illustration the exemplary the x-ray grid alignment circuit 100 for coupling the x-ray grid assembly 90 to the detector 14. As shown in FIG. 7, the alignment circuit 100 includes at least one marker 102 that is configured to be mounted to the x-ray grid assembly 90 and generate an alignment signal based on a position of the marker 102. The alignment circuit 100 also includes at least one sensor 104 that is mounted to the x-ray detector 14 and an alignment module 106 that is configured to receive the alignment signal from the sensor 104 and utilize the alignment signal to determine if the x-ray grid assembly 90 is coupled to a detecting face 60 of the detector 14.

Figure 8A:
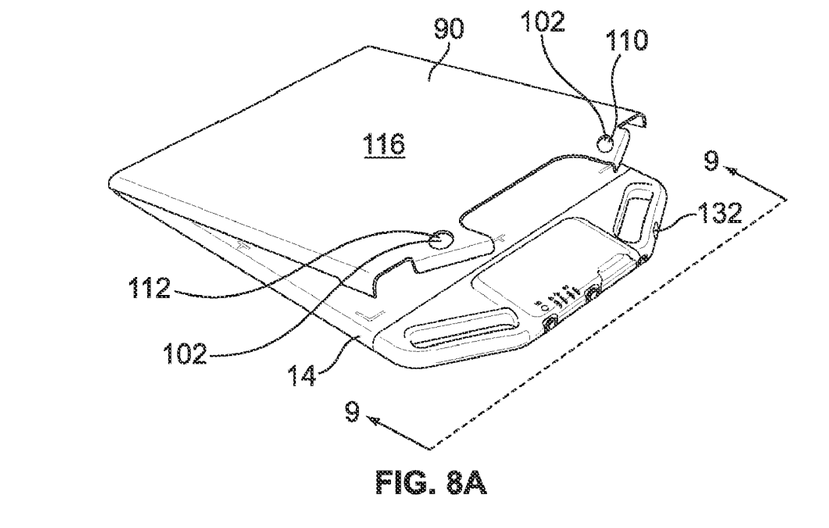
FIG. 8A is a top perspective view of the detector and the x-ray grid assembly partially coupled to the detector in accordance with an embodiment of the present invention.
Figure 8B:
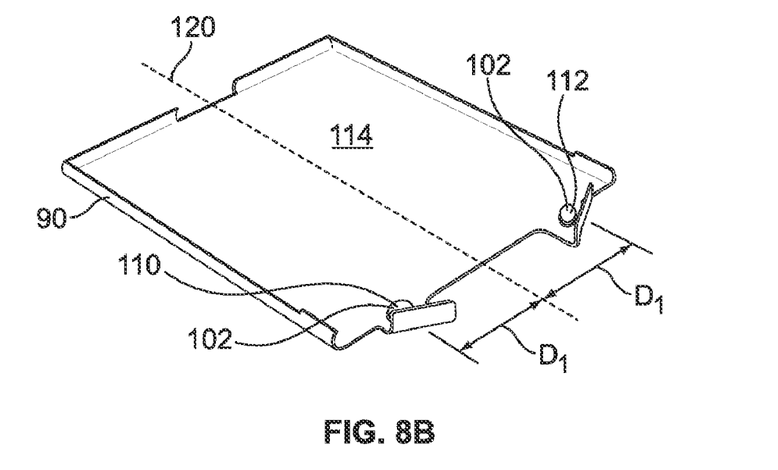
FIG. 8B is a bottom perspective view of the x-ray grid assembly shown in FIG. 8A.

FIG. 8A is a top perspective view of the detector 14 and the x-ray grid assembly 90 partially coupled to the detector 14. FIG. 8B is a bottom perspective view of the x-ray grid assembly 90. During assembly, the marker 102 is mounted to the x-ray grid assembly 90 as shown in FIGS. 8A-8B. In one embodiment, the marker 102 may be coupled to the x-ray grid holder 91. Optionally, the marker 102 may be mounted to the x-ray grid 93.

Figure 9:
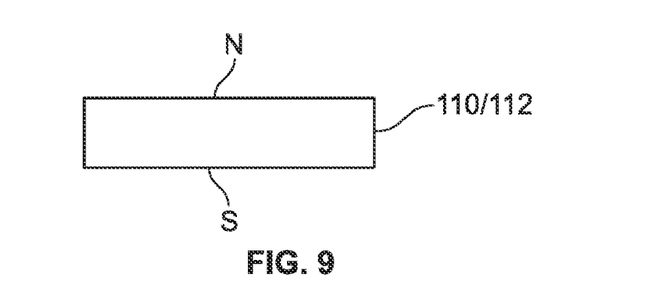
FIG. 9 is a side view of an exemplary marker in accordance with an embodiment of the present invention.

In the exemplary embodiment, the x-ray grid alignment circuit 100 includes a first marker 110 and a second marker 112. As shown in FIG. 9 each marker, in the exemplary embodiment, is embodied as a magnetic disc. Optionally, magnets having other shapes may be utilized. As shown in FIG. 9, each marker 110/112 includes a north magnetic pole (N) and a south magnetic pole (S) that is located on an opposing surface from the north pole (N). During operation, the magnets 110/112 produce a magnetic field that is utilized by the sensor 104 as discussed in more detail below. In the exemplary embodiment, the magnets 110/112 are embodied as disc magnets having a cylindrical cross-sectional profile. The markers 110/112 may be fabricated from any suitable ferromagnetic material, such as iron, nickel, cobalt, rare earth metals, or some other type of ferromagnetic alloy, for example. Optionally, the magnets 110/112 may be embodied as electromagnets. In another option, the markers may be other devices than magnets, such as push switches for example. Moreover, although the exemplary embodiment describes an alignment circuit that includes a single sensor 104 and a pair of markers 110 and 112, it should be realized that additional sensors or markers may be utilized. Moreover, the locations of the markers and the sensors may be determined based on the type of x-ray grid and detector being utilized.

Referring again to FIGS. 8A and 8B, in the exemplary embodiment, the marker 110 is coupled to the x-ray grid 90 such that the north magnetic pole (N) is disposed facing the detector 14. The marker 112 is coupled to the x-ray grid 90 such that the south magnetic pole (S) is facing the detector 14. In the exemplary embodiment, the magnets 110/112 are coupled to the x-ray grid 90 such that a polarity of the marker 110 facing the detector 14 is opposite to the polarity of the marker 112 facing the detector 14. More specifically, the magnets 110/112 are coupled to the x-ray grid 90 such that a polarity of the marker 110 facing the detector 14 is opposite to a polarity of the marker 112 facing the detector 14. In another exemplary embodiment, the magnets 110/112 are coupled to the x-ray grid 90 based on the strength of the magnets. For example, the magnet 110 may have a magnetic strength X whereas the magnet 112 has a strength 2X. The single sensor 104 may then detect the strength of the magnet facing the sensor, and based on the strength, determine if the x-ray grid is properly coupled to the detector 14.

As shown in FIG. 8B, to couple the marker 110 to the x-ray grid 90, the marker 110 is positioned a distance $D_1$ from a centerline 120 of the x-ray grid 90. Moreover, the marker 112 is also positioned the distance $D_1$ from the centerline 120 on an opposite side of the x-ray grid 90. As such, the magnets 110 and 112 are positioned on opposite sides of the x-ray grid 90 and symmetrical with respect to the centerline axis 120. The magnets 110/112 may then be affixed to the x-ray grid 90 using an adhesive for example. Positioning the magnets 110/112 symmetrical with respect to the centerline axis 120 enables the sensor 104 to be substantially aligned with the marker 110 when the x-ray grid 90 is coupled to the detecting face 60 of the detector 14. Moreover, when the x-ray grid 90 is incorrectly coupled to the back cover 62 of the detector 14, the sensor 104 is substantially aligned with the marker 112.

In the exemplary embodiment, the sensor 104 is configured to determine a polarity or strength of the marker 110/112 when the sensor 104 is substantially aligned with either marker 110 or 112. As such, the sensor 104 includes a first detecting surface 130 and an opposing second detecting surface 132. In the exemplary embodiment, the sensor 104 is configured to generate a first alignment signal when the first detecting surface 130 detects a magnetic north pole, e.g. when sensor 104 determines that the marker 110 is substantially aligned with the sensor 104. Moreover, the sensor 104 is configured to generate a second alignment signal when the second detecting surface 132 detects a magnetic south pole, e.g. when sensor 104 determines that the marker 112 is substantially aligned with the sensor 104. In this manner, the sensor 104 determines which marker 110 or 112 is substantially aligned with the sensor 104 and thus determines whether the x-ray grid assembly 90 is coupled to the detecting face 60 or the back cover 62 of the detector 14.

For example, the sensor 104 is configured to determine whether the marker 110 or 112 has either a north magnetic pole (N) facing the sensor 104 or a south magnetic pole (S) facing the sensor 104. As discussed above, the marker 110 is coupled to the x-ray grid 90 such that the north magnetic pole (N) is disposed facing the detector 14. The marker 112 is coupled to the x-ray grid 90 such that the south magnetic pole (S) is facing the detector 14. By determining the polarity or strength of the marker 110 or 112 currently aligned with the sensor 104, the sensor 104 is able to identify whether the sensor 104 is aligned with either the marker 110 or the marker 112.

Referring again to FIG. 7, as discussed above, the x-ray grid alignment circuit 100 also includes an alignment module 106 that is configured to receive the alignment signal from the sensor 104 and utilize the alignment signal to determine if the x-ray grid assembly 90 is coupled to a detecting face 60 of the detector 14. As discussed above, the alignment signal may include the first alignment signal, the second alignment signal, or no alignment signal. The alignment module 106 may be embodied as a software program that is installed on the processor 82. Optionally, the alignment module 106 may be implemented as a hardware device. During operation, the alignment module 106 is configured receive the alignment signal from the sensor 104 and utilize the alignment signal to determine if the x-ray grid assembly 90 is coupled to the detecting face 60 of the detector 14.

Figure 10A:
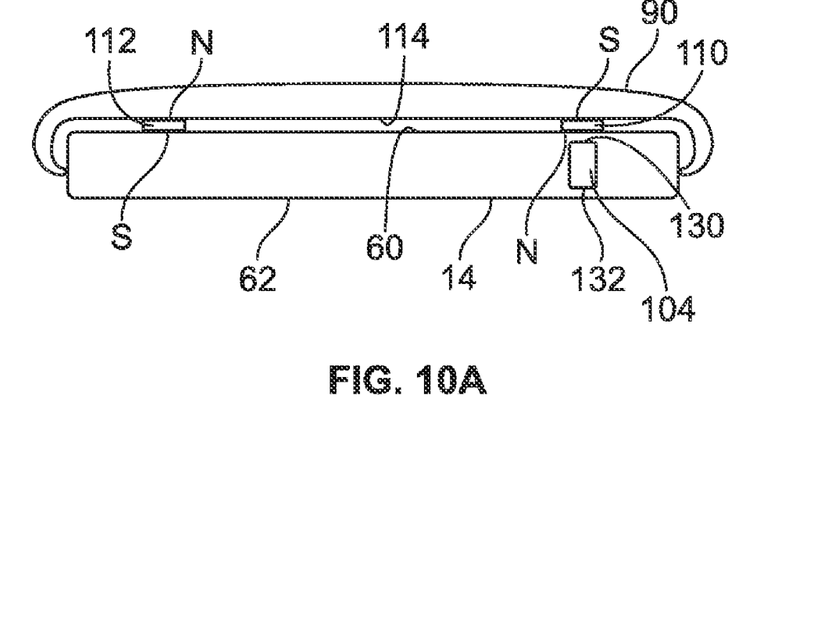
FIGS. 10A and 10B are top and bottom perspective views of the exemplary x-ray grid assembly coupled to an exemplary detector in accordance with an embodiment of the present invention.
Figure 10B:
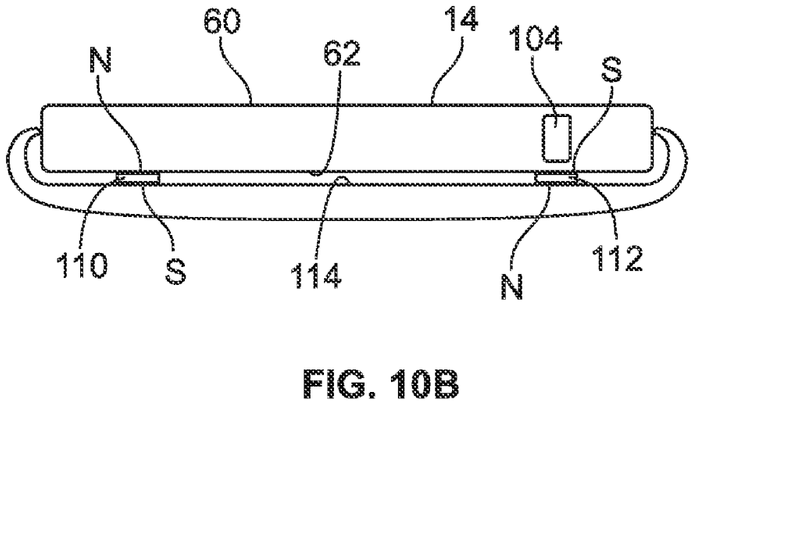

For example, FIG. 10A illustrates the x-ray grid assembly 90 correctly coupled to the detecting face 60 of the detector 14. FIG. 10B illustrates the x-ray grid assembly 90 coupled to the back cover 62 of the detector 14. As shown in FIG. 10A, to determine if the x-ray grid assembly 90 is coupled to the detecting face 60 of the detector 14, the sensor 104 determines a polarity or strength of the marker 110 or 112 being aligned with the sensor 104. If the x-ray grid 90 is properly coupled to the detecting face 60 of the detector 14, the sensor 104 will generate an alignment signal that indicates a north magnetic pole has been detected, e.g. the marker 110 is aligned with the detector 14. In this case, the alignment module 106 receives the alignment signal and generates an indication that the x-ray grid 90 is coupled to the detecting face 60.

The alignment module 106 also determines when the x-ray grid assembly 90, or the x-ray grid itself, is coupled to an opposing back surface 62 of the detector 14. As shown in FIG. 10B, to determine if the x-ray grid assembly 90 is coupled to the back cover 62 of the detector 14, the sensor 104 determines a polarity or strength of the marker 110 or 112 being aligned with the sensor 104. If the x-ray grid 90 is incorrectly coupled to the back cover 62 of the detector 14 as shown in FIG. 10B, the sensor 104 will generate an alignment signal that indicates a south magnetic pole has been detected, e.g. the marker 112 is aligned with the detector 14. In this case, the alignment module 106 receives the alignment signal and generates an indication that the x-ray grid 90 is coupled to the back cover 62. Based on this indication, the operator can remove the x-ray grid assembly 90 from the back cover 62 and coupled the x-ray grid assembly 90 to the detecting face 60.

In another embodiment, the alignment module 106 also determines when the x-ray grid assembly 90 is not coupled to the detector 14. In this case, when the alignment module 106 does not receive a signal from the sensor 104, the alignment module 106 generates an alignment signal that indicates that the x-ray grid assembly 90 is not coupled to the detector 14.

During operation, the x-ray grid alignment module 106 transmits the alignment signal, either correctly aligned, incorrectly aligned, or no x-ray grid assembly 90 installed, over a wireless communication link to a remote workstation. In one embodiment, the alignment signal indicating that the x-ray grid is coupled to the detecting face, an opposing back surface of the detector, or not coupled to the detector is utilized by the detector 14 to generate an indication that is observable at the detector 14. In another embodiment, the alignment signal is transmitted wirelessly to a remote location. In one embodiment, the alignment signal is transmitted from the transceiver 44 to the transceiver 46 such that the system controller 26 receives the alignment signal. The system controller 26 may then utilize the alignment signal as discussed below. In another embodiment, the alignment signal is transmitted from the transceiver 44 to the transceiver 48 such that the work station 34 receives the alignment signal. The work station 34 may then utilize the alignment signal as discussed below.

As discussed above, the x-ray grid alignment module 106 transmits the alignment signal, either correctly aligned, incorrectly aligned, or no x-ray grid assembly 90 installed. Based on the received alignment signal, the alignment module 106 is configured to activate an indicator to inform an operator of the alignment status of the x-ray grid assembly. The indication may be an audio indication wherein different audio signals are generated based on whether the x-ray grid assembly 90 is coupled to the detecting face 60, the back cover 62, or not coupled to the detector 14.

In the exemplary embodiment, the alignment module 106 generates a visual indication that represents the alignment status of the x-ray grid assembly 90. In one embodiment, the detector 14 includes at least one visual indicating device 140 that is activated based on the alignment signal. For example, when the x-ray grid assembly 90 is coupled to the detecting face 60, the indicating device 140 may emit light having a first color, e.g. green. When the x-ray grid assembly 90 is coupled to the back cover 62, the indicating device 140 may emit light having a different second color, e.g. red. In a further embodiment, when the x-ray grid assembly 90 is not coupled to the detector 14, the indicating device 140 may emit light having a different third color, e.g. yellow. Optionally, the detector may include several light indicating devices 140 that each indicate an alignment status of the x-ray grid. For example, a first indicating device emits a green light, a second indicating device emits a yellow light, and a third indicating device emits a red light. Moreover, as discussed above, the alignment signal may be transmitted to the system controller 26 and/or the workstation 34. Therefore, the system controller 26 includes a visual indicator 142 and the workstation 34 includes a visual indicator 144. In the exemplary embodiment, the visual indicators 142 and/or 144 may be visual indicators that are displayed on a display device such as display 40 shown in FIG. 2. In each case, the visual indicators 140, 142, and 144 provide a visual indication that the x-ray grid assembly 90 is coupled to the detecting face 60, the back cover 62, or not coupled to the detector 14.

During operation, the system controller 26 or the workstation 34 also utilizes the alignment signal received from the detector 14 to determine a scan protocol. For example, one scan protocol may be selected when the alignment signal indicates that the x-ray grid 90 is properly coupled to the detecting face 60 of the detector 14. Another different scan protocol may be selected when the alignment signal indicates that the x-ray grid 90 is in correctly coupled to the back cover 62 of the detector 14 or when the x-ray grid assembly 90 is not coupled to the detector 14. Moreover, the visual indicator warns the operator in an acquisition screen, e.g. display 40, to re-attach the x-ray grid assembly 90 and also inhibits the operation of the x-ray source 12 until the x-ray grid assembly 90 is coupled to the detecting face 60 of the detector 14.

Referring again to FIG. 7, the system 10 also includes a scan protocol database 150. The scan protocol database 150 is configured to store a plurality of scan protocols that may be utilized by the system 10. In use, the scan protocol is selected based on the alignment signal. For example, if the x-ray grid assembly 90 is coupled to the detecting face 60 a first scan protocol may be selected. Optionally, if the x-ray grid assembly 90 is coupled to the back cover 62 or not coupled to the detector 14 a second scan protocol may be selected. The different scanning protocols include for example, modifying the duration of a scan acquisition, modifying a detector configuration, modifying the quantity of gates used to collect the imaging data, and/or modifying the type of scan acquisition, for example.

In the exemplary embodiment, the above described the x-ray grid alignment circuit for coupling an x-ray grid to a detector and method of fabricating the alignment circuit may be used separately or in combination. A technical effect of the alignment circuit is to detect the presence and proper alignment of an x-ray grid installed on a portable detector. Moreover, the alignment circuit because the x-ray grid assembly is necessary in some examinations to reduce x-ray scattering even though the amount of dose has to be significantly higher, the dose level with the x-ray grid assembly can be several times higher as that without the x-ray grid assembly. The alignment circuit there enables an operator to make decisions and select to select x-ray techniques based to properly manage patient dosage.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray grid alignment system for coupling an x-ray grid to a detector, the x-ray grid alignment system comprising:
    a marker configured to be mounted to the x-ray grid;
    a sensor configured to be mounted to the detector, the sensor generating an alignment signal based on a position of the marker; and
    an alignment module configured to receive the alignment signal from the sensor and utilize the alignment signal to determine when the x-ray grid is coupled to a detecting surface of the detector and inhibit the operation of an x-ray source based on the alignment signal.

2. An x-ray grid alignment system in accordance with claim 1, wherein the alignment module is further configured to determine when the x-ray grid is not coupled to the detector.

3. An x-ray grid alignment system in accordance with claim 1, wherein the alignment module is further configured to transmit the alignment signal over a wireless communication link to a remote workstation, the wireless alignment signal indicating that the x-ray grid is coupled to the detecting surface, an opposing non-detecting surface of the detector, or not coupled to the detector.

4. An x-ray grid alignment system in accordance with claim 1, wherein the alignment module is further configured to transmit the alignment signal to a remote workstation, the remote workstation determining a scan protocol based on the alignment signal.

5. An x-ray grid alignment system in accordance with claim 1, further comprising a visual indicator, the alignment module activating the visual indicator when the x-ray grid is coupled to the detecting surface of the detector.

6. An x-ray grid alignment system in accordance with claim 1, wherein the marker comprises a magnet coupled to the x-ray grid, the sensor generating the alignment signal based on a polarity of the magnet.

7. An x-ray grid alignment system in accordance with claim 1, wherein the marker comprises a magnet coupled to the x-ray grid, the sensor generating the alignment signal based on a strength of the magnet.

8. An x-ray grid alignment system in accordance with claim 1, wherein the x-ray grid alignment system further comprises a second marker coupled to the x-ray grid, the alignment module configured to activate a visual indicator when the x-ray grid is coupled to an opposing non-detecting surface of the detector based on the second marker.

9. An x-ray grid alignment system in accordance with claim 1, wherein the alignment module is further configured to inhibit the operation of the x-ray source when the x-ray grid is coupled to an opposing non-detecting surface of the detector.

10. An x-ray grid alignment system in accordance with claim 1, wherein the alignment module is further configured to prompt an operator to couple the x-ray grid to the detecting surface of the detector when the x-ray grid is coupled to an opposing non-detecting surface of the detector.

11. An x-ray grid alignment system for coupling an x-ray grid to a detector, the x-ray grid alignment system comprising:
    a marker configured to be mounted to the x-ray grid;

a sensor configured to be mounted to the detector, the sensor generating an alignment signal based on a position of the marker; and an alignment module configured to receive the alignment signal from the sensor and utilize the alignment signal to determine when the x-ray grid is coupled to a detecting surface of the detector and when the x-ray grid is coupled to an opposing back non-detecting surface of the detector.

12. An x-ray grid alignment system for coupling an x-ray grid to a detector, the x-ray grid alignment system comprising:

a marker configured to be mounted to the x-ray grid;

a sensor configured to be mounted to the detector, the sensor generating an alignment signal based on a position of the marker; and an alignment module configured to receive the alignment signal from the sensor and utilize the alignment signal to determine when the x-ray grid is coupled to a detecting surface of the detector and to activate a visual indicator on a remote workstation when the x-ray grid is coupled to the detecting surface of the detector, when the x-ray grid is coupled to an opposing non-detecting surface of the detector, and when the x-ray grid is not coupled to the detector.

13. A detector assembly comprising:

a portable detector;

an x-ray grid configured to be mounted to the portable detector; and an x-ray grid alignment system for coupling the x-ray grid to the portable detector, the x-ray grid alignment system comprising a marker configured to be mounted to the x-ray grid;

a sensor configured to be mounted to the portable detector, the sensor generating an alignment signal based on a position of the marker; and an alignment module configured to receive the alignment signal from the sensor and utilize the alignment signal to determine when the x-ray grid is coupled to a detecting surface of the portable detector and to prompt an operator to couple the x-ray grid to the detecting surface of the portable when the x-ray grid is coupled to an opposing non-detecting surface of the detector.

14. A detector assembly in accordance with claim 13, wherein the alignment module is further configured to determine when the x-ray grid is coupled to the opposing non-detecting surface of the detector and when the x-ray grid is not coupled to the opposing non-detecting surface of the detector.

15. A detector assembly in accordance with claim 13, wherein the alignment module is further configured to transmit the alignment signal over a wireless communication link to a remote workstation, the wireless alignment signal indicating that the x-ray grid is coupled to the detecting surface, the opposing non-detecting surface of the detector, or not coupled to the portable detector.

16. A detector assembly in accordance with claim 13 wherein the alignment module is further configured to transmit the alignment signal to a remote workstation, the remote workstation determining a scan protocol based on the alignment signal.

17. A detector assembly in accordance with claim 13 further comprising a visual indicator, the alignment module activating the visual indicator when the x-ray grid is coupled to the detecting surface of the portable detector.

18. A detector assembly in accordance with claim 13 wherein the alignment module is configured to activate a visual indicator on a remote workstation when the x-ray grid is coupled to the detecting surface of the detector, when the x-ray grid is coupled to the opposing non-detecting surface of the detector, and when the x-ray grid is not coupled to the detector.

19. A detector assembly in accordance with claim 13 wherein the marker comprises a magnet, the sensor generating the alignment signal based on a polarity of the magnet.

20. A detector assembly in accordance with claim 13 wherein the marker comprises a magnet, the sensor generating the alignment signal based on a strength of the magnet.

21. A detector assembly in accordance with claim 13 wherein the x-ray grid alignment system further comprises a second marker coupled to the x-ray grid, the alignment module configured to activate a visual indicator when the x-ray grid is coupled to the opposing non-detecting surface of the detector based on the second marker.

22. A method for coupling an x-ray grid to a portable detector, the method comprising:

providing a marker configured to be mounted to an x-ray grid;

providing a sensor configured to be mounted to the portable detector, the sensor generating an alignment signal based on a position of the marker;

determining when the x-ray grid is coupled to a detecting surface of the portable detector based on the alignment signal;

inhibiting the operation of an x-ray source based on the alignment signal; and displaying an indication on a display when the x-ray grid is coupled to the detecting surface of the portable detector.

23. A method in accordance with claim 22 further comprising:

determining when the x-ray grid is coupled to an opposing non-detecting surface of the detector and notifying a user that the x-ray grid is mounted to the opposing non-detecting surface of the detector.

24. A method in accordance with claim 22 further comprising determining a scan protocol based on the alignment signal.

* * * * *

UNITED STATES PATENT AND TRADEMARK OFFICE
CERTIFICATE OF CORRECTION

| | |
|---|---|
| PATENT NO. | : 8,172,461 B2 |
| APPLICATION NO. | : 12/550881 |
| DATED | : May 8, 2012 |
| INVENTOR(S) | : Liu et al. |

It is certified that error appears in the above-identified patent and that said Letters Patent is hereby corrected as shown below:

In Column 13, Line 8, in Claim 11, delete "opposing back non-detecting" and insert -- opposing non-detecting --, therefor.

Signed and Sealed this
Thirteenth Day of November, 2012

David J. Kappos
*Director of the United States Patent and Trademark Office*